United States Patent
Van Der Wal et al.

(10) Patent No.: US 11,622,862 B2
(45) Date of Patent: Apr. 11, 2023

(54) IMPLANT, FITTING PLATE AND METHOD OF MANUFACTURING AN IMPLANT AND FITTING PLATE

(71) Applicants: UMC UTRECHT HOLDING B.V., Utrecht (NL); UNIVERSITEIT UTRECHT HOLDING B.V., Utrecht (NL)

(72) Inventors: Bart Cornelis Hendrikus Van Der Wal, Amersfoort (NL); Ralph Johan Bernard Sakkers, Loenen aan de Vecht (NL); Björn Petrus Meij, Bilthoven (NL); Lucas Alphonsus Maria Evers, Zeist (NL); Hermanus Hendricus Weinans, Driebergen-Rijsenburg (NL)

(73) Assignees: UMC UTRECHT HOLDING B.V., Utrecht (NL); UNIVERSITEIT UTRECHT HOLDING B.V., Utrecht (NL)

( * ) Notice: Subject to any disclaimer, the term of this patent is extended or adjusted under 35 U.S.C. 154(b) by 1086 days.

(21) Appl. No.: 16/301,778

(22) PCT Filed: May 30, 2017

(86) PCT No.: PCT/NL2017/050346
§ 371 (c)(1),
(2) Date: Nov. 15, 2018

(87) PCT Pub. No.: WO2017/209605
PCT Pub. Date: Dec. 7, 2017

(65) Prior Publication Data
US 2019/0151098 A1 May 23, 2019

(30) Foreign Application Priority Data

May 31, 2016 (NL) ..................... 2016867

(51) Int. Cl.
*A61F 2/30* (2006.01)
*A61B 34/10* (2016.01)
*A61F 2/32* (2006.01)

(52) U.S. Cl.
CPC ............ *A61F 2/30942* (2013.01); *A61F 2/32* (2013.01); *A61B 2034/102* (2016.02);
(Continued)

(58) Field of Classification Search
CPC ......... A61F 2/32; A61F 2/30942; A61B 34/10
See application file for complete search history.

(56) References Cited

U.S. PATENT DOCUMENTS 5,176,711 A 1/1993 Grimes
2010/0274534 A1* 10/2010 Steines ............... A61F 2/30942
703/11

(Continued)

FOREIGN PATENT DOCUMENTS

WO 2011156504 A2 12/2011
WO 2015052586 A2 4/2015
WO 2016044352 A1 3/2016

OTHER PUBLICATIONS

International Search Report and Written Opinion from PCT/NL2017/050346 dated Oct. 5, 2017, pp. 17.

*Primary Examiner* — Brian A Dukert
(74) *Attorney, Agent, or Firm* — KDB Firm PLLC

(57) ABSTRACT

An implant, a fitting plate suitable for placing of an implant, and a method for manufacturing an implant suitable for application on one or more bones.

16 Claims, 8 Drawing Sheets

(52) U.S. Cl.
CPC ... *A61B 2034/105* (2016.02); *A61B 2034/108* (2016.02); *A61F 2002/3096* (2013.01); *A61F 2002/30736* (2013.01)

(56) References Cited

U.S. PATENT DOCUMENTS

| | | |
|---|---|---|
| 2015/0250552 A1 | 9/2015 | Radermacher et al. |
| 2017/0249440 A1* | 8/2017 | Lang ................ B22F 10/80 |

* cited by examiner

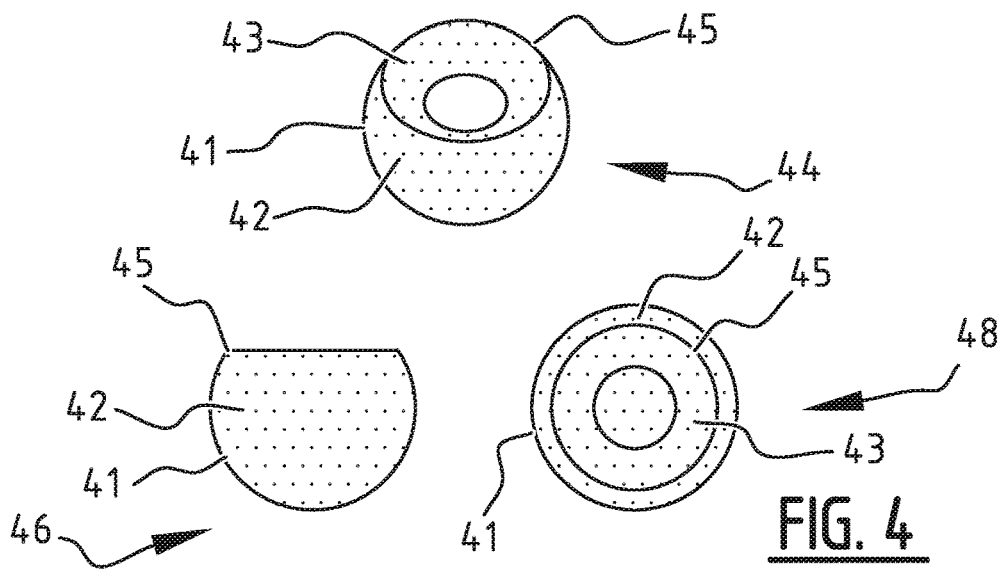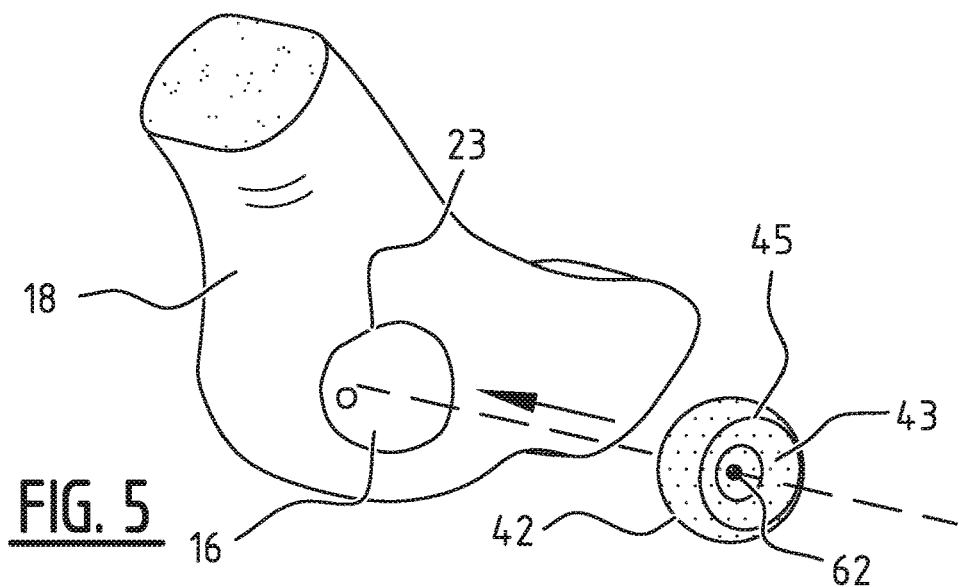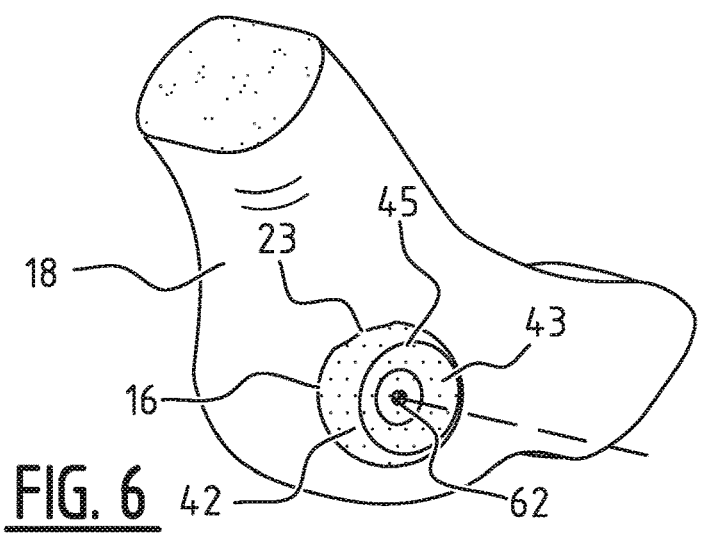

IMPLANT, FITTING PLATE AND METHOD OF MANUFACTURING AN IMPLANT AND FITTING PLATE

This is a national stage application filed under 35 U.S.C. § 371 of pending international application PCT/NL2017/050346 filed May 30, 2017, which claims priority to Netherlands Patent application NL 2016867, filed May 31, 2016, the entirety of which applications are hereby incorporated by reference herein.

Implants are usually applied in order to replace bones or parts of bones or to support or reinforce damaged bones. An example of a disorder wherein implants are applied in some treatments is hip dysplasia, a usually congenital underdevelopment of the hip joint occurring inter alia in humans and dogs. Hip dysplasia is characterized in that the hip socket (acetabulum), which forms the socket in which the head of the thigh bone (femoral head or femur head) is situated, is too shallow. The pressure on the femoral head is hereby distributed in insufficiently uniform manner, with the common result of peak loads on parts of the femoral head and acetabular rim, which may cause, among other things, premature wear of the hip joint. In respect of hip dysplasia, diagnosis, medical imaging and surgical therapy are very similar for humans and dogs.

According to the present patent application, a method is provided of manufacturing an implant suitable for application on one or more bones, the method comprising of:
  providing a data set of at least a part of each of the one or more bones;
  creating a model of the one or more bones on the basis of the data set;
  defining in the model a range of motion of the one or more bones within predetermined boundaries;
  positioning a model of an implant with predetermined shape in the model of the one or more bones, wherein a first rotation point of the model implant is placed at a most probable position in the model of the one or more bones;
  modifying the positioned model implant by removing parts of the model implant which overlap the model of the one or more bones;
  simulating movements of the model of the one or more bones with the modified model implant, wherein the simulated movements are encompassed by the defined range of motion of the one or more bones in the model;
  selecting parts of the model implant which during the simulation limit the simulated movements which cause the defined range of motion not to be reached;
  further modifying the model implant by removing the selected parts;
  manufacturing the further modified model implant so that the implant is obtained.

The method according to the present patent makes it possible to obtain an implant which precisely matches the shape of the one or more bones of the patient, for instance a human or dog, for which the implant is manufactured. This has the advantage that it becomes possible, among other things, to minimize removal or shaving off of pieces of bone, or other modifications to the bone.

It will be apparent that the presence of cartilage, capsule, synovial membrane and so on is taken into consideration during performing of the method. Parts of the further modified model implant which remain but are undesired, for instance parts with a volume which is too small, can in addition be removed from the model implant.

In addition, the method has the advantage that the implant is designed using movement simulations of the one or more bones, whereby possible undesired impingements or jamming of movements due to the implant can be avoided. Possible impingements of the freedom of movement due to deformations of one or more of the bones can also be prevented.

Usually applied surgical treatments of hip dysplasia, such as the shelf procedure and a shape of a single or multiple pelvic osteotomy with the purpose of tilting the acetabulum, do not have the advantages of the above stated method. In the shelf procedure an additional piece of bone is arranged on the acetabulum in order to further cover the femoral head, wherein the additional bone is usually taken from another bone of the patient. The pelvic osteotomy is characterized by detaching the acetabulum from the pelvis and rotating the acetabulum such that the femoral head is covered more, particularly on the weight-bearing upper side. It is particularly this latter surgical therapy which has the drawback of being highly invasive, wherein side effects such as numbness and pain, among others, can occur.

In both treatments a further drawback is that the precision of both the reconstruction of the acetabulum and the determination of a correctly fitting coverage of the femoral head (acetabular coverage) are limited. This can have the result that movements of the joint are impinged, for instance due to too much acetabular coverage. It is also possible that the acetabulum is not sufficiently modified to imperfections of the femoral head. This can cause, among other things, a reduced freedom of movement of the hip joint of the patient and/or insufficient acetabular coverage. It will be apparent that said drawbacks in respect of the treatment of hip dysplasia can also occur in treatments of other disorders of bones and joints.

The implant is preferably suitable for application in a joint comprising two or more bones, wherein the two or more bones are movably connected to each other. Simulating the movements in the joint avoids possible impingements by the bones moving relative to the one or more bones with the implant. The step of selecting can here be the selection of parts of the model implant which overlap the two or more bones during simulation of the simulated movements.

The implant is preferably suitable for application on an acetabulum and suitable for at least partially receiving a femoral head, wherein the model of the one or more bones comprises a model of at least the acetabulum and a model of at least the femoral head, wherein the method further comprises of:
  positioning the model of the femoral head in the model of the acetabulum with model implant, wherein a second rotation point of the model of the femoral head is placed at the most probable position in the model of the acetabulum with model implant. This preferred embodiment is particularly suitable for application in hip dysplasia, wherein the acetabulum covers the femoral head insufficiently.

Playing a part in respect of undesired impingements in implants which are applied in the hip joint are, among other things, impingements of the femoral head, connected via the femur neck to the femur, by an acetabulum with implant. If the acetabulum with implant covers too great a surface area of the femoral head, movements of the femur may possibly be limited. These are referred to as impingements of the pincer type. Another common impingement is an impingement of the cam type, i.e. an impingement wherein due to irregularities in the femur neck the femur is impinged more easily by the acetabulum enlarged by the implant. The femur neck is the part of the femur which connects the femoral head to the femur.

The implant is preferably suitable for application on at least an upper side of the acetabulum, wherein the implant extends at least partially from the acetabulum, thereby forming an extension of the acetabulum. It is hereby possible to realize an extension of the upper side or roof of the acetabulum in a relatively non-invasive manner. This is because the upper side of the acetabulum bears the most force.

The implant preferably comprises a first and a second implant body, wherein the first implant body is suitable for application on the acetabulum and the second implant body is suitable for application on, or as, the femoral head. In some cases, particularly when the implant substantially replaces the acetabulum, it can be preferred also to provide the femoral head with an implant body in order to prevent accelerated wear, among other things.

The steps of modifying, selecting and further modifying are preferably only performed for the first implant body of the implant. If the femoral head is also replaced, the second implant body can have substantially the same shape as the femoral head of the patient. The modifying, selecting and further modifying need hereby only be applied to the first implant body.

The method preferably further comprises steps of determining a coverage of the femoral head by the acetabulum with further modified model implant and modifying the acetabular coverage by modifying the model implant when the determined coverage does not fall within predetermined boundaries. Although the method provides for a correctly fitting implant in respect of the range of motion of the joint and the surface of the acetabulum with implant covering the femoral head, it is preferred to compare the acetabulum with the further modified model implant to healthy, comparable hips, for instance of the patient's other side or known comparable anatomy. Possible values for comparison are the Norberg angle and the center-edge (CE) angle, as further elucidated with reference to FIG. 12-14. If simulation of movements within the defined range of motion results in the implant being reduced in size such that the acetabular coverage falls outside desired values of for instance the Norberg angle and center-edge angle, the coverage can be enlarged. This will generally be the case when, due to irregularities in the femur neck, femoral head and/or femur, the femur and the implant model overlap sooner during the simulated movements.

The model of the one or more bones and the model implant is preferably three-dimensional. This has the advantage that the movement simulation can be performed in multiple directions.

All steps are preferably performed using computer hardware and software. This has the advantage that the method can be performed at least partially autonomously by the computer.

The data set preferably comprises at least in part data from the group comprising x-rays, computed tomography scans (CT scan), magnetic resonance imaging (MRI) and the like, as will be known to the skilled person. When x-rays are used, x-rays taken from multiple angles relative to the one or more bones should preferably be available in order to increase the accuracy of the model of the one or more bones.

The shape of the model implant is preferably predetermined subject to, among other things, the one or more bones on which the implant is to be applied, on the basis of data of the patient, comprising the data set and the model of the one or more bones and/or data of the one or more comparable healthy bones. It is here possible to envisage characteristic values for the one or more bones, such as diameter, but also age, gender and so on of the patient. In respect of an implant suitable for a hip it is possible to use for instance, among other values, the diameter, shape and/or other characteristic values of the femoral head and/or acetabulum.

In the step of positioning, the most probable position of the first rotation point is preferably substantially equal to a position of a second rotation point of a second bone comprised by the joint. In respect of for instance an implant suitable for application on the acetabulum it is preferred for the position of the first rotation point of the model implant to be equal to that of a second rotation point of the femoral head: the position around which the femoral head rotates, i.e. the position of the femoral head which, during movement, has the smallest expected change in position relative to the model acetabulum with model implant. The first rotation point of the model implant can therefore also be situated outside the model implant.

The positioning is further preferably done on the basis of characteristics of a healthy, comparable joint of the patient him/herself or of healthy, comparable reference joints. In the case of an implant applicable for a hip the data set can also comprise characteristic values of the hip, such as the size and position of the centre of the femoral head and the like.

The range of motion is preferably defined on the basis of characteristics of the patient, for instance age, the range of motion of a healthy comparable bone or joint such as the other hip of the patient, if possible, and specific deformations of the bone on which the implant is applied. Data of healthy comparable joints can also be used.

The method preferably further comprises of designing fastening means of the implant to be fastened to the one or more bones, comprising one or more of screw holes, screws (with or without head), self-tapping screws, self-locking screws, pins and so on, subject to available space, an expected loading of the implant and/or suitability of parts of the one or more bones.

The step of simulating movements of the model of the one or more bones with the modified model implant preferably further comprises of simulating a loading of the model implant. This step has the advantage, among others, that both the implant and the fastening means can be suitably designed, with inter alia sufficient strength. By manufacturing the implant according to the method the surface of the part of the implant which will be fastened to the bone of the patient will be substantially complementary to the fastening location of the model of the bone predetermined with imaging, so that a correct location and fit of the implant is obtained.

The method preferably further comprises of:
creating a model of a fitting plate comprising a surface which is substantially equal to a surface of the further modified model implant facing the bone, wherein the surface of the further modified model implant facing the bone is adjacent to the model of the one or more bones;
arranging one or more perforations in the model fitting plate at a predetermined position on the fitting plate and in a predetermined direction, wherein some of the perforations are on the one hand suitable for making open connections through the cortex and to the underlying medullary cavity in order to enhance the ingrowth of bone into the implant for placing, and some of the perforations are on the other hand suitable to prepare the implant for receiving fastening means; and manufacturing the model fitting plate so that a fitting plate is obtained.

The fitting plate has the shape of the surface of the implant which is adjacent to the bone of the patient to which the implant has to be fastened. It is hereby possible to find the correct location for the implant during placing of the manufactured implant, because it fits only the part of the bone with the same surface. In addition, the fitting plate comprises inter alia perforations at the locations where screws have to be placed in the bone, in order to guide the drilling. These perforations are preferably provided with screw thread (for instance 3.5 mm) in which drill guides can be fixed. The perforations preferably have a predetermined direction, depending on the direction in which the screw has to be placed in the bone of the patient, wherein the direction is determined by the imaging/model of the bone of the patient, as also elucidated with reference to the fastening means.

The implant is preferably manufactured from a biofunctional material, wherein the biofunctional material is manufactured from materials which comprise titanium and/or magnesium, and which are preferably porous. Optionally porous titanium and titanium alloys have the advantage, among others, that they may stimulate regeneration and/or growth of the bone. The biofunctionality can further be stimulated by application of a surface treatment of the titanium with bioactive substances or growth factors and/or the implant can be filled with biomaterials such as hydrogels, loaded with cells, bioactive compounds or growth factors. This stimulates the growth of the cartilage, the growth of the bone and/or the integration of the implant with the surrounding bone, among other things. Materials which are also possible for the implant are materials which dissolve slowly, such as materials on the basis of magnesium. If the implant also serves as a site/substrate for new cartilage and bone to grow, the implant itself will have become unnecessary after a determined period of time, and soluble materials can be used.

Manufacturing of the implant is preferably done by three-dimensional printing. Use is also made of the term additive manufacturing, among others, in order to indicate that an object, in this case the implant, is built up of smaller parts, such as metal powder. The object is for instance built up layer by layer, which can be an advantageous way of manufacturing the implant, since it is designed specifically for each patient.

According to the present patent application, an implant is further provided which is suitable for application on one or more bones, comprising a first implant body, the first implant body comprising:
  a first side with a shape corresponding substantially to the shape of one or more first sides of at least one of one or more model bones in a model of the one or more bones;
  a second side with a shape corresponding substantially to a shape of one or more second sides of at least one of the one or more model bones; and
  at least one implant rim connecting the first side to the second side;
  wherein the first side, the second side and the implant rim are configured such that the one or more model bones are free of movement limitation during simulations of movements within a defined range of motion of the one or more model bones.

The implant is preferably suitable for application on an acetabulum of a pelvis and suitable for at least partially receiving a femoral head, wherein the one or more first sides comprise one or more sides of a model of the pelvis and/or the acetabulum, wherein the one or more second sides comprise a curved outer side of a model of the femoral head.

The second side, which covers at least a part of the model of the femoral head, preferably has an acetabular coverage which falls within the predetermined boundaries.

According to the present patent application, a fitting plate is further provided which serves to prepare the surface for placing of an implant at a predetermined suitable location, the fitting plate comprising:
  a fitting side with a shape corresponding substantially to a first side of the implant, wherein the first side is configured such that one or more model bones wherein the implant is applied are free of movement limitation during simulations of movements within a defined range of motion of the one or more model bones;
  one or more perforations at a predetermined position on the fitting plate and in a predetermined direction, wherein some of the perforations are suitable for making open connections through the cortex and to the underlying medullary cavity, and one or more perforations are suitable to prepare for receiving fastening means on the implant for placing; and
  an engaging side with means to be engaged by and/or connected to a device suitable for this purpose.

Further advantages, features and details of the present invention will be elucidated on the basis of the following description of figures relating to a preferred embodiment thereof, in which:

FIG. 4 shows a model implant with predetermined shape in various views;

FIG. 5 shows the positioning of the model implant in the acetabulum;

FIG. 6 shows the positioned model implant in the acetabulum;

Figure 1A:
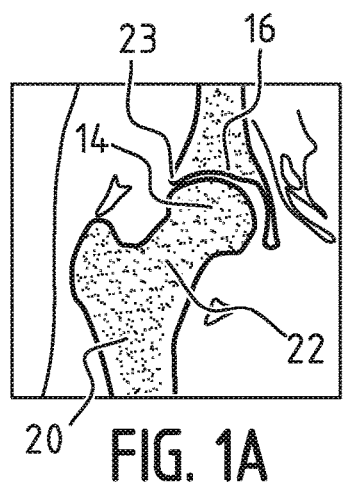
FIG. 1A shows an exemplary x-ray image of a hip joint comprising the femoral head and acetabulum in a coronal section.
Figure 1B:
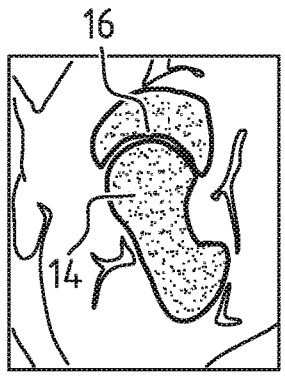
FIG. 1B shows an exemplary x-ray image of the hip joint comprising the femoral head and acetabulum in a sagittal diagonal section.
Figure 1C:
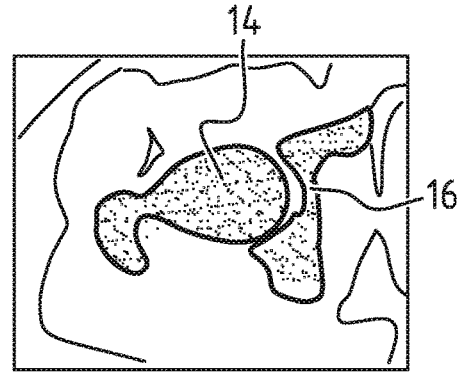
FIG. 1C shows an exemplary x-ray image of the hip joint comprising the femoral head and acetabulum in a transverse section.

FIG. 1A-C show graphic data of for instance a CT scan, wherein a femur 20 comprising a femur neck 22 and a femoral head 14 is visible in coronal section in FIG. 1A. An acetabulum 16 with acetabular rim 23 is also visible. A coronal section is understood to mean a section along a plane dividing a human or animal body into a front and a rear side, wherein this coronal plane is parallel to the longitudinal axis of the body. The sagittal section of FIG. 1B is understood to mean a section along the sagittal plane, which divides the body into two unequal left-hand and right-hand parts. A transverse section as in FIG. 1C is understood to mean a cross-section perpendicularly of the longitudinal axis of the body.

Figure 2A:
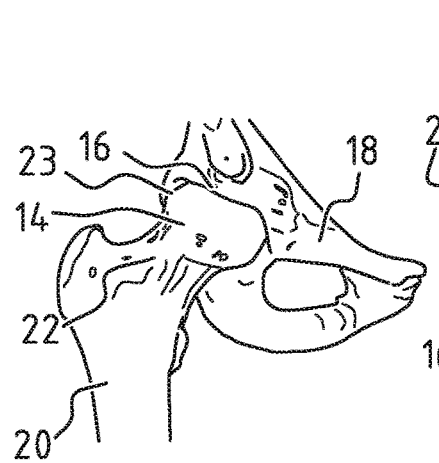
FIG. 2A shows a model seen in coronal direction of the hip joint comprising a part of the femur with femoral head and pelvis with acetabulum created on the basis of data of the hip joint.
Figure 2B:
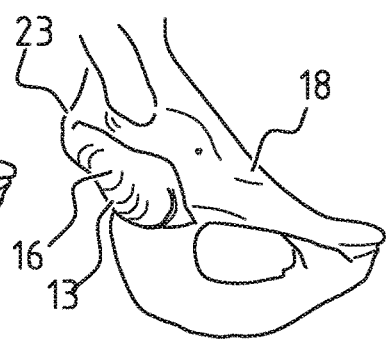
FIG. 2B shows the model of the pelvis with acetabulum of FIG. 2A.
Figure 2C:
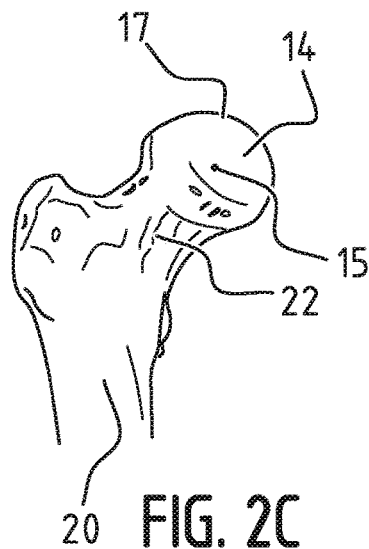
FIG. 2C shows the model of the femur with femoral head of FIG. 2A.

A model of, among other things, femoral head 14 and acetabulum 16 with acetabular rim 23 as shown in FIG. 2A-C is constructed on the basis of a data set comprising the exemplary data shown in FIGS. 1A, 1B and 1C. The model on the basis of the data set further also comprises a part of a pelvis 18. The model preferably takes a three-dimensional shape. The models of pelvis 18 with acetabulum 16 and femur 20 are modelled as individual parts on the basis of the data set, so that they can be moved relative to each other. The model of femur 20 shown in the view of FIG. 2C comprises femoral head 14 with femoral rotation point 15. The femoral rotation point 15 is understood to mean the position around which the femoral head rotates, i.e. the position of the femoral head which, during rotation, has the smallest expected change in position relative to the model acetabulum with model implant. Femoral head 14 further comprises a first curved outer side 17 with a determined shape, for instance with several irregularities. Cup-shaped inner side 13 of acetabulum 16 also has a determined shape, where irregularities, among other things, can also occur.

The method, including creation of the model, is preferably performed virtually by means of computer hardware and software.

Figure 3:
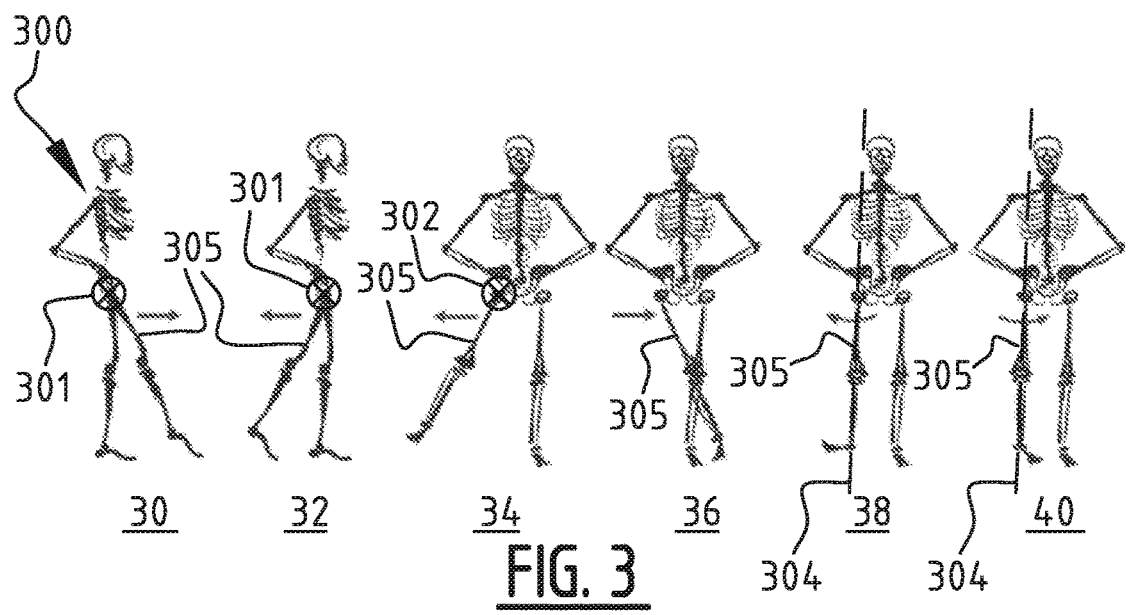
FIG. 3 is a view of a model of a human skeleton showing movements of the hip joint about various axes.

FIG. 3 shows possible directions of movement of the hip joint, wherein in a model 300 of a human skeleton the hip joint is rotatable about a first axis 301 in side views 30 and 32 by respectively a forward movement and a rearward movement (respectively flexion and extension) of leg 305. First axis 301 is substantially perpendicular relative to a sagittal plane of, in this case, model 300.

A lateral movement outward (see front view 34) and inward (see front view 36, respectively abduction and adduction) of leg 305 results in rotation about a second axis 302 of the hip joint. Axis 302 for the right-hand hip joint and axis 303 for the left-hand hip joint is substantially perpendicular relative to a coronal plane of model 300.

Rotation of a leg outward in front view 38 (in clockwise direction as seen from the top of model 300, exorotation) and inward in front view 40 (counter-clockwise, endorotation) results in the hip joint rotating about a third axis 304 which extends along leg 305. These movements are applied in the following simulation of movements of the model.

A range of motion is defined on the basis of, among other things, the model of the one or more bones as can be seen in FIG. 2, preferably further on the basis of characteristics of the patient, for instance age, the range of motion of a healthy comparable bone or joint such as the other hip of the patient, if available, and specific deformations of the bone on which the implant is applied. Data of healthy, comparable joints can also be used.

FIG. 4 shows a model of an implant 42 with predetermined shape in perspective view 44, side view 46 and top view 48. Model implant 42 comprises an outer side 41, a curved inner side 43 and model implant rim 45. As stated above, the shape in this starting state of model implant 42 and, with this, the second curved outer side 41 also depends on the one or more bones on which the implant is to be applied, on the basis of data of the patient comprising the data set and the model of the one or more bones and/or data of the one or more comparable healthy bones. It is possible here to envisage characteristic values for the one or more bones, such as diameter, but also the age, the gender and so on of the patient. In respect of an implant suitable for a hip it is possible to use, among other values, the diameter, shape and/or other characteristic values of the femoral head and/or acetabulum.

Figure 15:
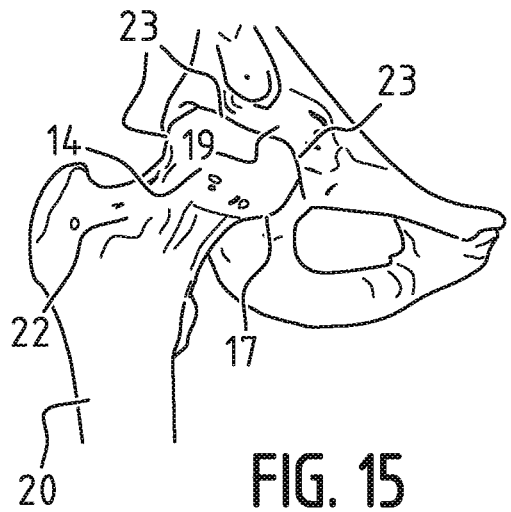
FIG. 15 shows a model in coronal view of the hip joint comprising the femoral head and acetabulum created on the basis of data of the hip joint in which the femoral head is insufficiently covered.
Figure 16:
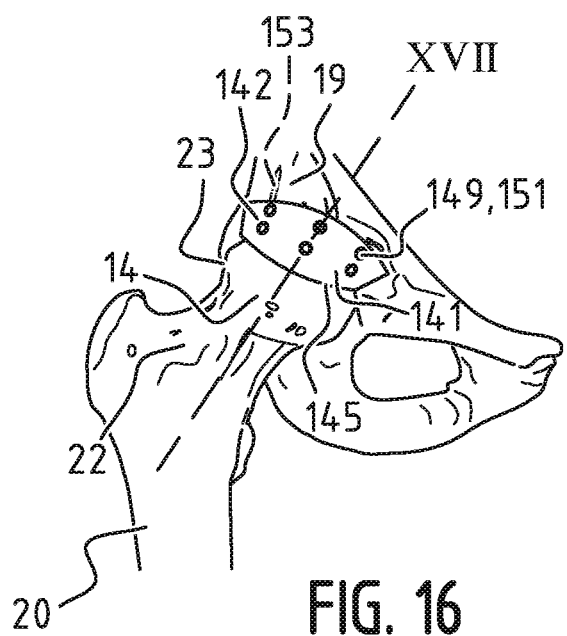
FIG. 16 shows the model of FIG. 15 in which the femoral head is also covered by the model implant.
Figure 17:
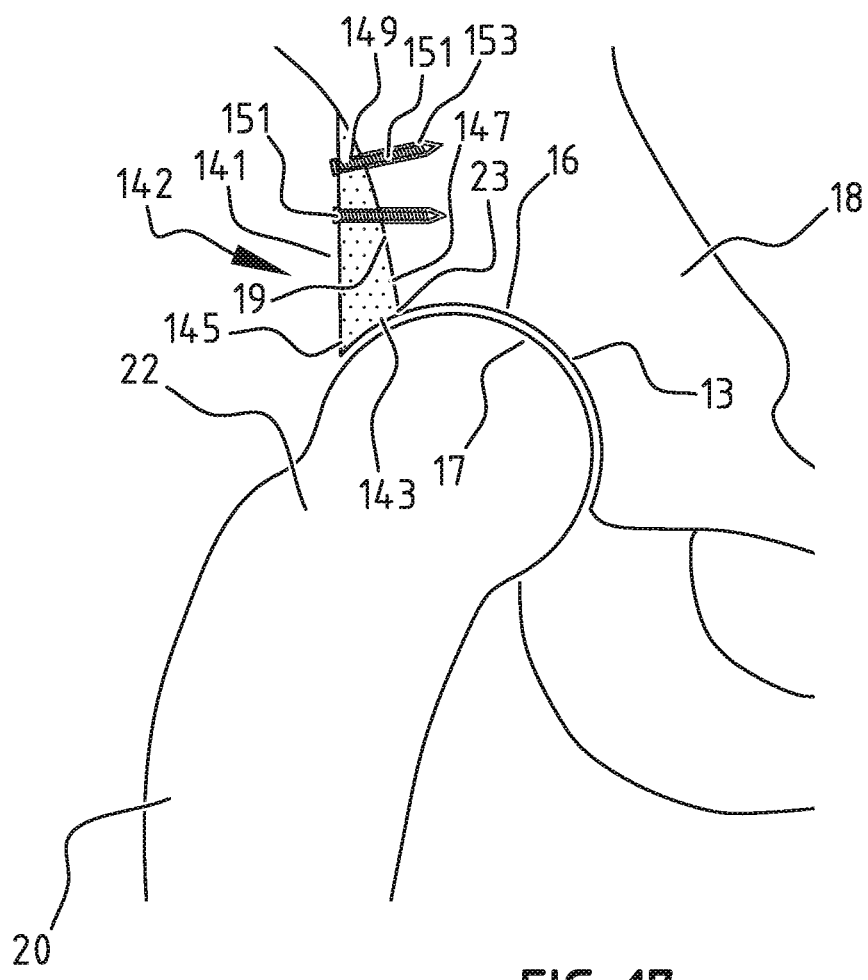
FIG. 17 shows the model of the hip joint with model implant of FIG. 16 in cross-section along the line designated with XVII.

The positioning of model implant 42 is shown schematically in FIG. 5. Model implant 42 is moved toward acetabulum 16 with acetabular rim 23 so that a rotation point 62 of model implant 42 is placed at the most probable position in acetabulum 16. The most probable position of rotation point 62 can for instance correspond to the femoral rotation point 15 of the femoral head determined in FIG. 2. Model implant 42 is shown in the final position in FIG. 6. As can be seen in FIG. 6, in this embodiment model implant 42 wholly covers acetabulum 16. It will be apparent that model implant 42 may also add to or replace only a part of acetabulum 16, such as the above mentioned extension of the upper side of acetabulum 16 along acetabular rim 23, in respect of which an example is shown in FIG. 15-17. The resulting implant depends on the specific joint, in this case a hip, for which the implant can be suitably applied.

Figure 7:
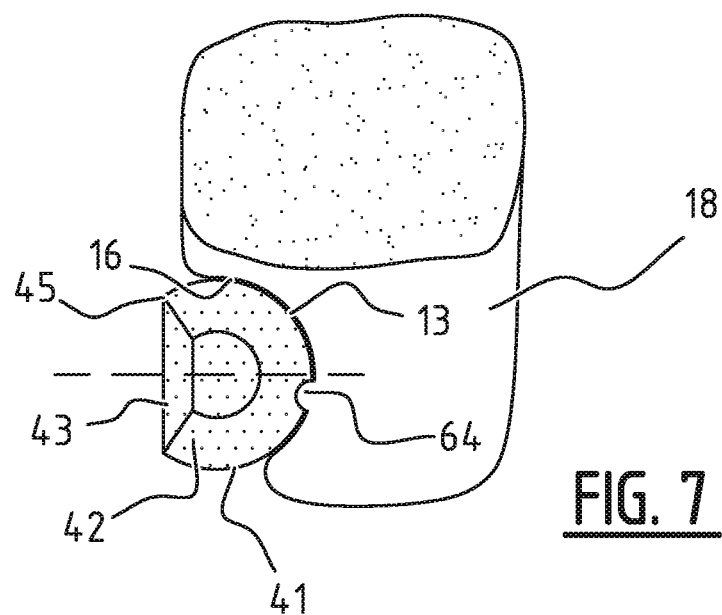
FIG. 7 shows the modified model implant positioned in an acetabulum with irregularities in a coronal section.

FIG. 7 is an example of the modification of the positioned model implant 42 shown in a cross-section. A part of the positioned model implant 42 overlaps irregularity 64 in the cup-shaped inner side 13 of acetabulum 16. Model implant 42 is modified by the removal of parts of the model implant which overlap the one or more bones, in this case acetabulum 16 and pelvis 18. In this example model implant 42 overlapped inter alia irregularity 64. By performing this step the curved outer side 41 of model implant 42 substantially follows the shape of the curved inner side 13 of acetabulum 16 in this example, whereby removal of bone, for instance by means of shaving, in order to allow the implant to fit can be avoided.

Although the irregularity is situated in the acetabulum in the example of FIG. 7, it is possible for at least a part of the model implant to overlap the pelvis outside the acetabulum. The part which overlaps the bone will there also be removed. Obtained hereby is a surface of the model implant adjacent to the side of the model of the pelvis with acetabulum which substantially corresponds to the adjacent surface of the pelvis with acetabulum.

Figure 8:
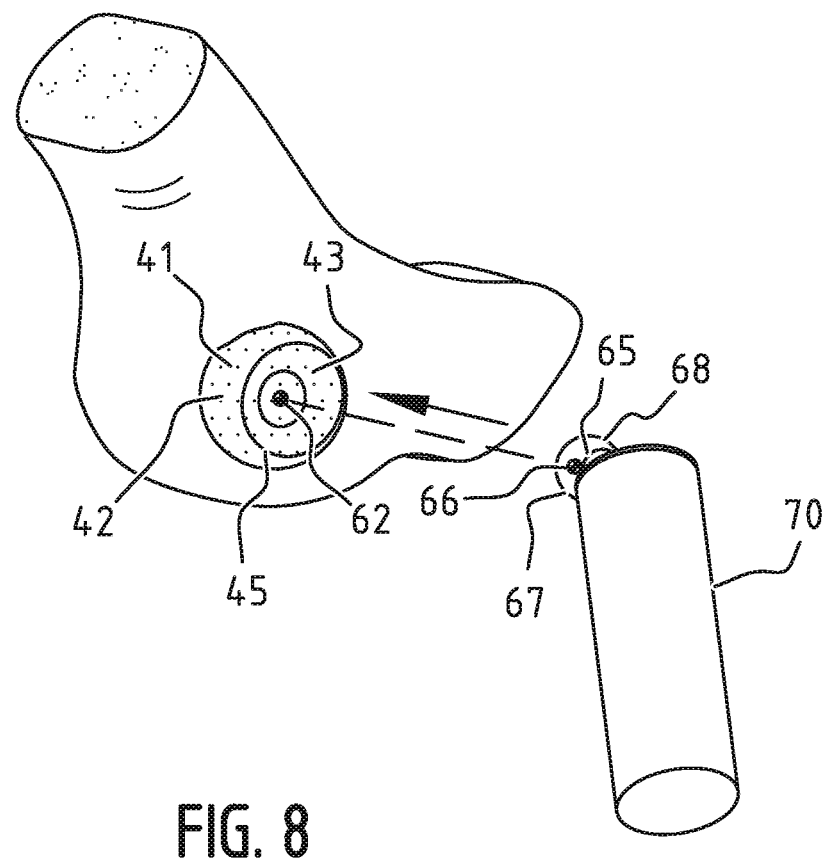
FIG. 8 is a perspective view of the positioning of the model of the femoral head with femur in the positioned model implant.

After model implant 42, in this example developed for a hip, has been positioned, the models of possible other bones which are comprised by the joint are positioned so that the movements can be simulated. As can be seen in FIG. 8, model femur 70 comprising model femoral head 68 and femoral head rotation point 66 is in this example positioned so that femoral head rotation point 66 is placed at the most probable position. Although model femur 70 is shown schematically, it may correspond to the created model of femur 20 (FIG. 2).

Another option is for model femur 70 to comprise at least partially a second model implant body. In this latter option model implant 42 would comprise a first model implant body and a second model implant body. The previous steps of positioning and modifying will then be performed for both model implant bodies.

Figure 9:
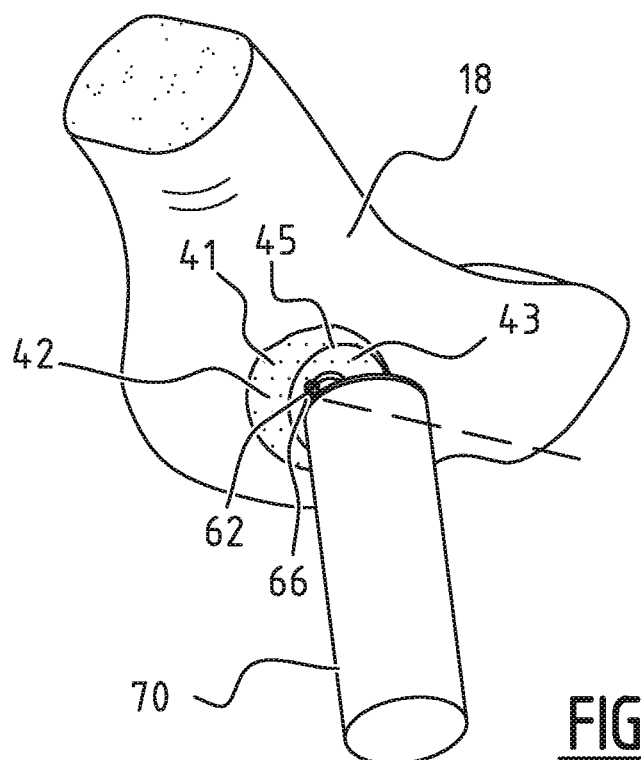
FIG. 9 is a perspective view of the positioned model of the femoral head.

This example is based on a model femur 70 which corresponds to the created model of femur 20, without second model implant body. Femoral head rotation point 66 and femoral head rotation point 15 of FIG. 2 thereby correspond. In this case third curved outer side 67 and first curved outer side 17 also correspond. During positioning of model femur 70 the most probable position can be determined by placing the position of femoral head rotation point 66 at the position of rotation point 62 of model implant 42, as can be seen in FIG. 9.

Figure 10:
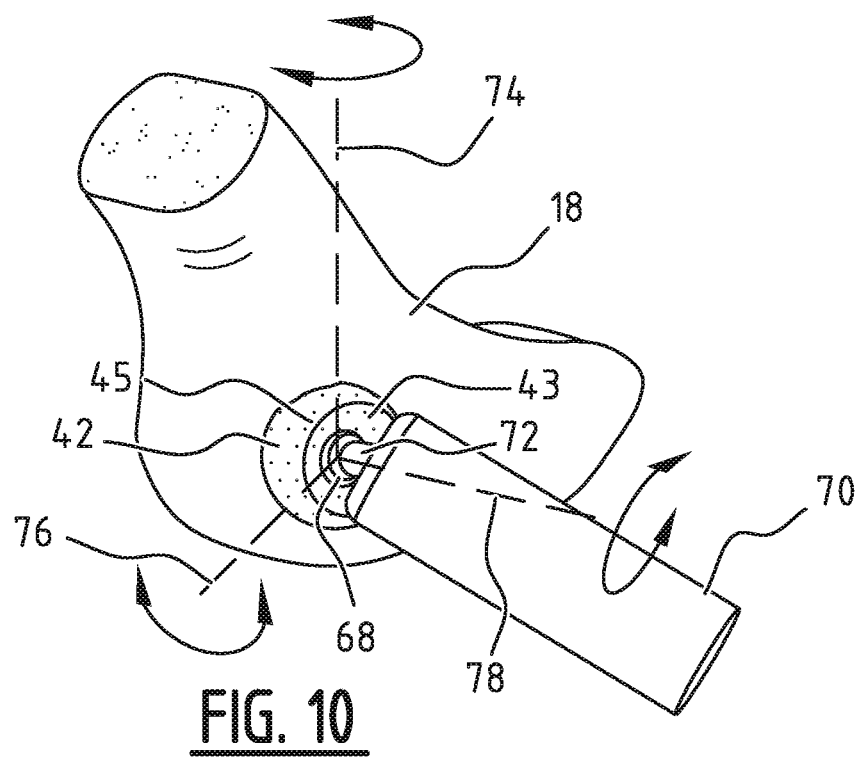
FIG. 10 is a perspective view of possible movements of the model of the hip joint with model implant which are encompassed by the simulations.

After model femur 70 has been positioned, movements of the model and the joint, comprising the model of the hip, model implant 42 and the model of model femur 70, are simulated. FIG. 10 shows rotations around three axes, wherein the axes correspond to the axes defined in FIG. 3. Axes 74, 76 and 78 correspond to respectively the first axis 301, second axis 302 and third axis 304 of FIG. 3. During the simulated movements femur neck 72 will for instance overlap parts of model implant 42, wherein these parts of model implant 42 are selected for removal.

Figure 11:
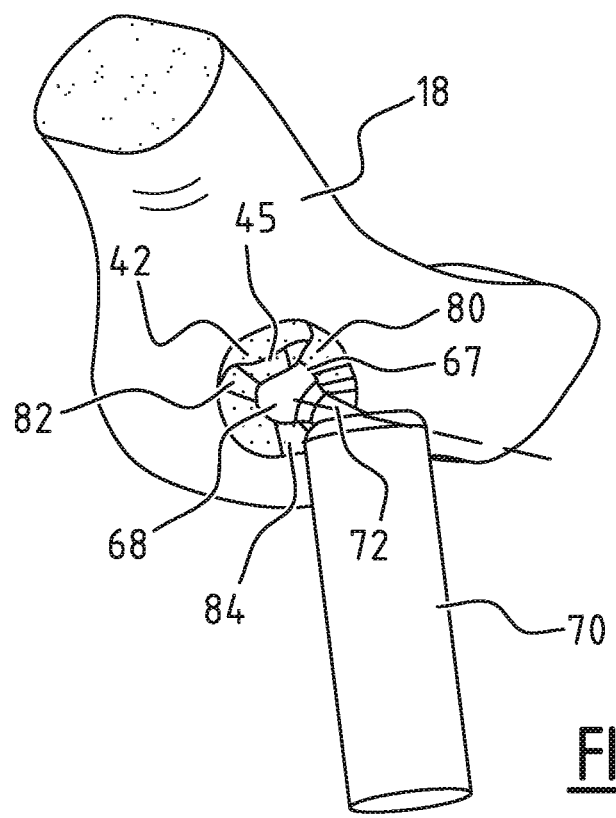
FIG. 11 is a perspective view of the further modified model implant on the model of the hip joint, wherein parts of the model implant have been removed.

FIG. 11 shows the further modified model implant 42, wherein the selected parts have been removed. These removed parts are visible in this example as recesses 80, 82 and 84, among others. By removing the selected parts of model implant 42, the curved inner side 43 is also modified to the third curved outer side 67 in all simulated positions. This reduces the possible limitation by the final implant manufactured from further modified model implant 42 of model femur 70, and the range of motion falls within the predetermined boundaries.

Figure 13:
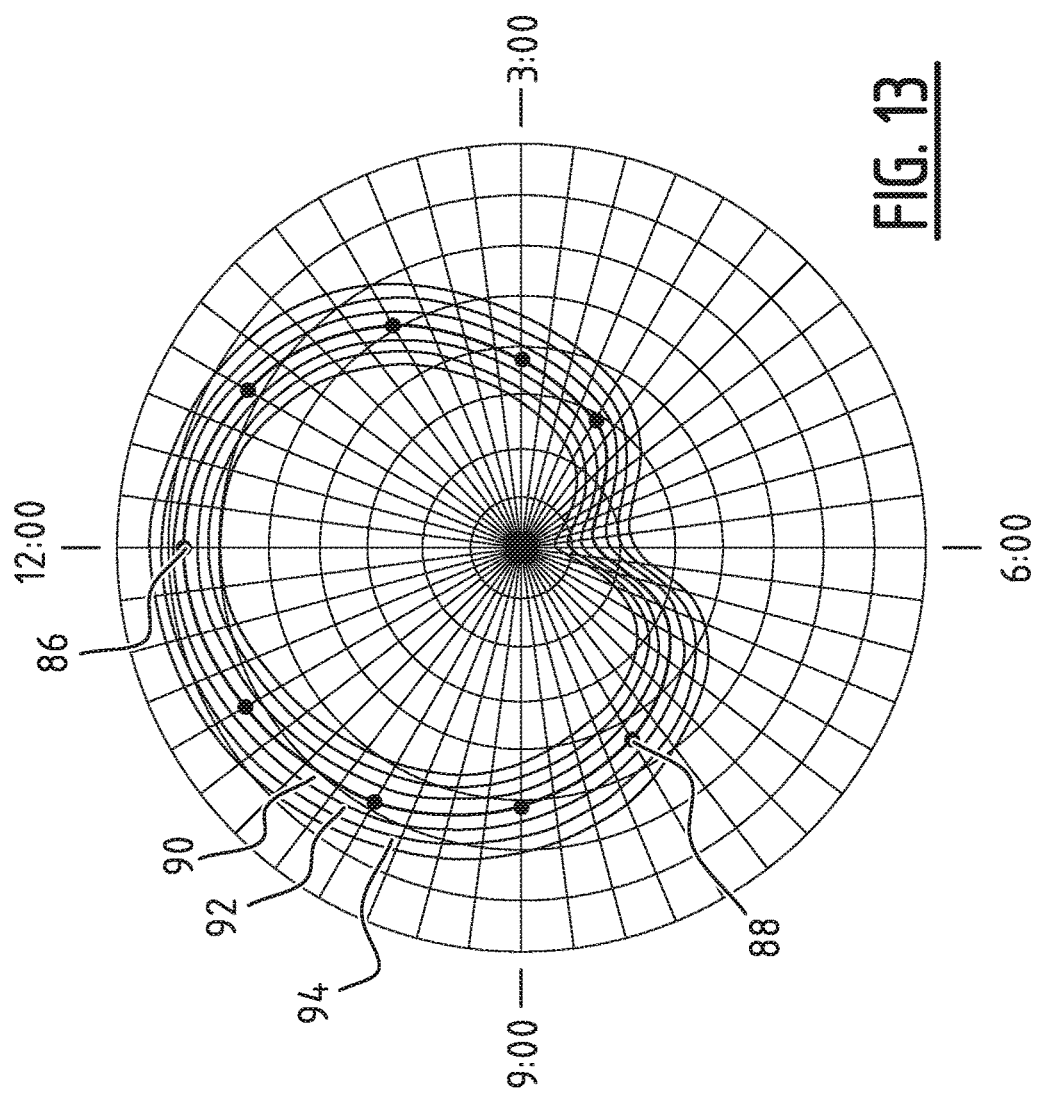
FIG. 13 shows exemplary measuring points of the coverage of the femoral head by the acetabulum with the model implant in the coordinate system of FIG. 12.
Figure 12:
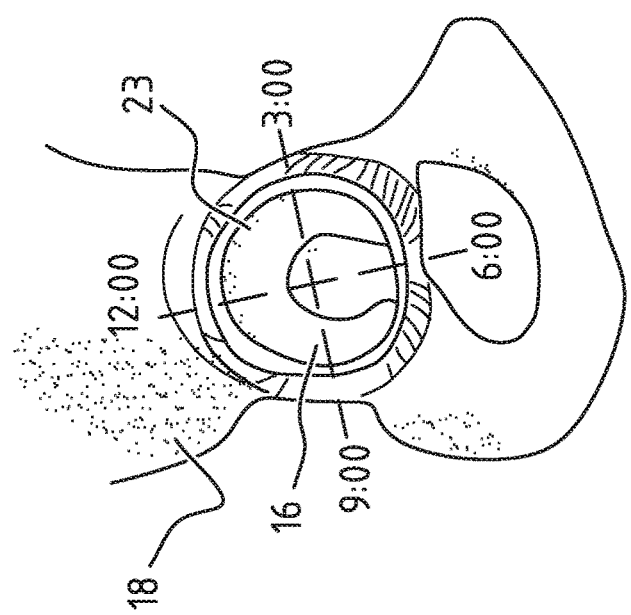
FIG. 12 is a coordinate system inside an acetabulum to show coverage of the femoral head by the acetabulum with model implant.
Figure 14:
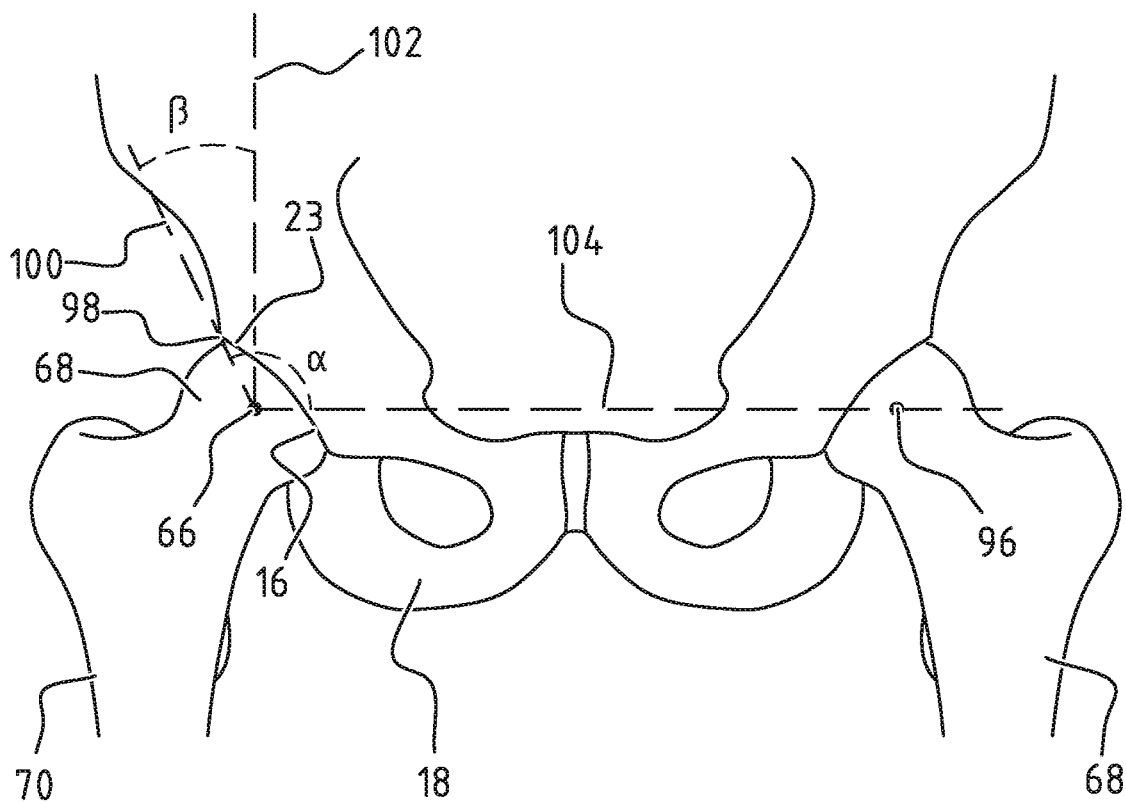
FIG. 14 is a pelvis in coronal view with two hip joints, showing two examples of measurements of coverage of the femoral head by the acetabulum with model implant.

FIGS. 12, 13 and 14 show schematic views of the determination of a coverage of femoral head 68 (not shown) by acetabulum 16 with further modified model implant 42 (not shown) and the modification of the coverage of femoral head 68 by the modification of the model implant when the determined coverage does not fall within predetermined boundaries. FIG. 12 shows two exemplary axes wherein clock positions 12:00, 3:00, 6:00 and 9:00 are shown, relative to which the coverage of the femoral head by acetabular rim 23 can be determined. An exemplary view of a determined coverage is shown in FIG. 13, wherein measuring point 86 for instance has a greater value for the coverage than measuring point 88. The upper part of acetabulum 16 and acetabular rim 23, corresponding to an average clock position of 12:00, must have a greater acetabular coverage than the lower part, corresponding to an average clock position of 6:00, because the weight is substantially supported by the upper part. The shown measuring points, such as measuring points 86 and 88, fall within indicated boundary area 90, which corresponds to a desired acetabular coverage.

FIG. 14 shows two examples of the determination of the coverage of femoral head 68 by acetabulum 16. The so-called Norberg angle is represented here by a, and the so-called center-edge (CE) angle by β. Determining of angle α is done, in this case in a front view of femur 70 positioned on acetabulum 16 at pelvis 18 with model implant 42 (not shown), by drawing a substantially straight line 100 from femoral head rotation point 66 to acetabular rim 23, in this case along upper acetabular rim 98. Angle α is the angle between line 100 and line 104, which is the connecting line between femoral head rotation point 66 and second femoral head rotation point 96. Angle β is the angle between line 100 and axis 102, which is substantially perpendicular relative to line 104. In the model of the one or more bones with model implant 42, this measurement can of course be performed along the whole acetabular rim 23 so that a plurality of measuring points as shown in FIG. 13 is obtained. It will also be apparent to the skilled person that similar measurements can be performed on bones and/or joints other than a hip.

FIG. 15 shows an example of a pelvis 18, a hip joint comprising femoral head 14 and acetabulum 16, as shown in FIG. 2. Acetabulum 16 with acetabular rim 23 covers femoral head 14 with curved outer side 17 insufficiently in this case. By performing the method according to the present patent a model implant 142 is obtained, which is substantially applicable along acetabular rim 23, as shown in FIG. 16 and, in cross-section along the line designated with XVII, in FIG. 17. The initial shape of model implant 142, which is not shown here, can be different than that of for instance FIG. 4. This is preferred in this case for obtaining a determined final shape.

Since acetabulum 16, at cup-shaped inner side 13, substantially covers the part situated therein of femoral head 14 with first curved outer side 17, model implant 142 is modified such that it is situated substantially along the upper side of acetabular rim 23. The curved inner side 143 follows first curved outer side 17 of femoral head 14, just as in FIG. 11. In this case outer side 141 has in part the shape of the model implant in the starting state. A side 147 of model implant 142 is formed by removing parts of the model implant which overlap the bone, in this case part 19 of a side of pelvis 18. By performing the method a surface of side 147 of the model implant facing the bone has a surface substantially complementary to the part 19 of pelvis 18 which is adjacent to model implant 142.

Model implant 142 further comprises fastening means, shown here as cylindrical holes 149 with a predetermined location and direction and screws 151 which are fastened in holes 153 in part 19 of pelvis 18.

A fitting plate is manufactured in order to place an implant manufactured on the basis of the model at the desired location inside the hip of the patient. A model of a fitting plate is created for this purpose, comprising a side substantially corresponding to the side of the implant which is situated on the pelvis, in FIG. 17 the side 147 of implant 142. The model fitting plate therefore fits with the side corresponding substantially to side 147 onto a determined location of the pelvis, in FIG. 17 on the pelvis above acetabular rim 23 on the surface of part 19 of pelvis 18.

The fitting plate has the shape of the surface of the implant which is adjacent to the bone of the patient to which the implant is to be fastened. This makes it possible to find the correct location for the implant during placing of the manufactured implant, as it fits only the part of the bone with the same surface. In addition, the fitting plate comprises perforations, wherein some of the perforations are suitable for making open connections through the cortex and to the underlying medullary cavity and some of the perforations are suitable to prepare for receiving fastening means on the implant for placing at the locations where screws have to be placed in the bone. In FIG. 17 these holes will be situated at the same location as holes 149 into which screws 151 are screwed.

The present invention is not limited to the above described preferred embodiments thereof; the rights sought are defined by the following claims, within the scope of which many modifications can be envisaged.

The invention claimed is:

1. A method of manufacturing an implant configured for application on one or more bones, the method comprising:
providing a data set of at least a part of each of the one or more bones;
creating a model of the one or more bones on the basis of the data set;
defining in the model a range of motion of the one or more bones within predetermined boundaries;
positioning a model of an implant with predetermined shape in the model of the one or more bones, wherein a first rotation point of the model implant is placed at a most probable position in the model of the one or more bones;
modifying the positioned model implant by removing parts of the model implant which overlap the model of the one or more bones;
simulating movements of the model of the one or more bones with the modified model implant, wherein the simulated movements are encompassed by the defined range of motion of the one or more bones in the model;
selecting parts of the model implant which during the simulation limit the simulated movements which cause the defined range of motion not to be reached;
further modifying the model implant by removing the selected parts; and
manufacturing the further modified model implant so that the implant is obtained.

2. The method according to claim 1, wherein the implant is configured for application in a joint comprising two or more bones, wherein the two or more bones are movably connected to each other.

3. The method according to claim 1, wherein the implant is configured for application on an acetabulum of a pelvis and to at least partially receive a femoral head, wherein the model of the one or more bones comprises a model of at least the acetabulum and a model of at least the femoral head, wherein the method further comprises:
positioning the model of the femoral head in the model of the acetabulum with model implant, wherein a second rotation point of the model of the femoral head is placed at the most probable position in the model of the acetabulum with model implant.

4. The method according to claim 3, wherein the implant is configured for application on at least an upper side of the acetabulum and extends at least partially from the acetabulum, thereby forming an extension of the acetabulum.

5. The method according to claim 3, wherein the implant comprises a first and a second implant body, wherein the first implant body is configured for application on the acetabulum and the second implant body is configured for application on, or as, the femoral head.

6. The method according to claim 5, wherein the steps of modifying, selecting and further modifying are only performed for the first implant body of the implant.

7. The method according to claim 3, further comprising:
determining a coverage of the femoral head by the acetabulum with further modified model implant; and
modifying the coverage of the femoral head by modifying the model implant when the determined coverage does not fall within predetermined boundaries.

8. The method according to claim 1, further comprising:
designing fastening means of the implant to be fastened to the one or more bones based on at least one of available space, an expected loading of the implant and suitability of parts of the one or more bones.

9. The method according to claim 8, further comprising:
creating a model of a fitting plate comprising a surface which is substantially equal to a surface of the further modified model implant facing the bone, wherein the surface of the further modified model implant facing the bone is adjacent to the model of the one or more bones;
arranging perforations in the model fitting plate at predetermined positions on the fitting plate and in a predetermined direction, wherein some of the perforations are configured to make open connections through the cortex and to the underlying medullary cavity, and some of the perforations are configured to prepare for receiving fastening means on the implant for placing; and
manufacturing the model fitting plate so that a fitting plate is obtained.

10. The method according to claim 9, wherein the perforations which serve to prepare for receiving the fastening means on the implant are substantially cylindrical and provided with a screw thread.

11. The method according to claim 10, wherein the model fitting plate is configured to make perforations for realizing open connections through the cortex and to the underlying medullary cavity and is also configured to prepare for placing of fastening means on the implant for placing.

12. The method according to claim 1, wherein simulating movements of the model of the one or more bones with the modified model implant further comprises simulating a loading of the model implant.

13. The method according to claim 1, wherein the implant is manufactured from a biofunctional material, wherein the biofunctional material is manufactured from materials comprising at least one of titanium and magnesium and which are porous.

14. The method according to claim 1, wherein the model of the one or more bones and the model implant are three-dimensional.

15. The method according to claim 1, wherein manufacturing of the implant is done by three-dimensional printing.

16. The method according to claim 1, wherein all steps are performed using computer hardware and software.

* * * * *